United States Patent [19]

Prestwich

[11] 4,452,793

[45] Jun. 5, 1984

[54] 29-FLUOROPHYTOSTEROL TERMITICIDES, COMPOSITIONS AND METHODS OF USE THEREFOR

[75] Inventor: Glenn D. Prestwich, Stony Brook, N.Y.

[73] Assignee: The Research Foundation of State University of New York, Albany, N.Y.

[21] Appl. No.: 470,819

[22] Filed: Feb. 28, 1983

[51] Int. Cl.³ .............................................. C07J 9/00
[52] U.S. Cl. .................................. 424/238; 260/397.2
[58] Field of Search ...................... 260/397.2; 424/238

[56] References Cited

FOREIGN PATENT DOCUMENTS 447212 5/1936 United Kingdom ............ 260/397.2

OTHER PUBLICATIONS

"Steroids" by Fieser et al., Reinhold Publishing Corp. (New York).

Primary Examiner—Elbert L. Roberts
Attorney, Agent, or Firm—Omri M. Behr

[57] ABSTRACT

29-Fluorophytosterols are utilized to form insecticidal and termiticidal compositions which are safe and economical for the combatting of termites and related insect pests.

25 Claims, 1 Drawing Figure

29-FLUOROPHYTOSTEROL TERMITICIDES, COMPOSITIONS AND METHODS OF USE THEREFOR

BACKGROUND OF THE INVENTION

Termites, and related insect pests, constitute a significant economic threat in a modern society. While conventional insecticides, typically chlorinated hydrocarbons such as chlordane, DDT, aldrin, dieldrin and BHC can be effectively utilized to eradicate these pests, such insecticides pollute water, contaminate soil, and are toxic to many life forms. Chlordane is the only chlorinated hydrocarbon that has not yet been banned, principally because a suitable substitute having its effectiveness has yet to be found. However, it still accumulates in the environment and causes food chain elimination since, for instance, an earthworm may be resistant to its poison, but the bird which consumes many such earthworms may die or be rendered infertile. An environmentally inactive chemical is thus needed to obviate food chain problems. While the chlorinated hydrocarbon insecticides are economical to product, the cost of the resulting environmental cleanup makes their use expensive in the long run. Thus, there exists a substantial need for new environmentally safe and effective pesticides.

One of the most distinctive areas of biochemical and physiological difference between insects and vertebrates is the steroid metabolism of insects. See, for instance, Svoboda and Thompson, "Comparative sterol metabolism in insects", p. 1-16; and Morisaki et al., "Sterol metabolism of the silkworm *Bombyx mori*", pp. 17-26; both in *Metabolic aspects of lipid Nutrition in Insects*, pp. 1-16, edited by Mittlerand Dadd, Westview Press, 1983;

Kircher, "Sterols and insects," in *Cholesterol Systems in Insects and Animals*, edited by Dupont pp. 1-50, CRC Press, 1982;

and Svoboda et. al., "Insect steroid metabolism," *Lipids* 13: 742-753 (1978).

Analogous to the use of pro-drugs in chemotherapy, pro-insecticides can be designed such that an insect enzyme converts a less toxic precursor into an inactivator of a specific protein. If the same protein catalytic site is involved in both unmasking and irreversible binding of a reactive species, then the pro-insecticide is considered to be a suicide substrate. See, for instance, Walsh, "Suicide substrates: mechanism-based enzyme inactivators", *Tetrahedron* 38: 871-909 (1982).

Fluoroactetate undergoes a "lethal synthesis" to α-fluorocitrate, which may either inhibit aconitase or a membrane-associated citrate transport protein. Insecticidal and other biocidal uses of fluoroacetate (or its metabolic precursors) previously received considerable attention many years ago, but most uses have been abandoned due to the inherently high toxicity of these compounds to vertebrates. (see, for instance, Pattison, *Toxic Aliphatic Fluorine Compounds*, Elsevier Press, 1959).

Utilizing the phytosterol dealkylation pathway unique to phytophagous insects, the latent poison fluoroacetate can be released in vivo. Additionally, it would be advantageous to release the fluoroacetate from a "masked" poison which could not be activated by vertebrates.

Most plant-eating insects degrade sitosterol (I) via fucosterol (II), fucosterol epoxide (III), and desmosterol (IV) to cholesterol (V). See, Scheme I below. Stigmasterol (VI) as degraded analogously via the cholestatrienol (VII). See, Scheme I, below:

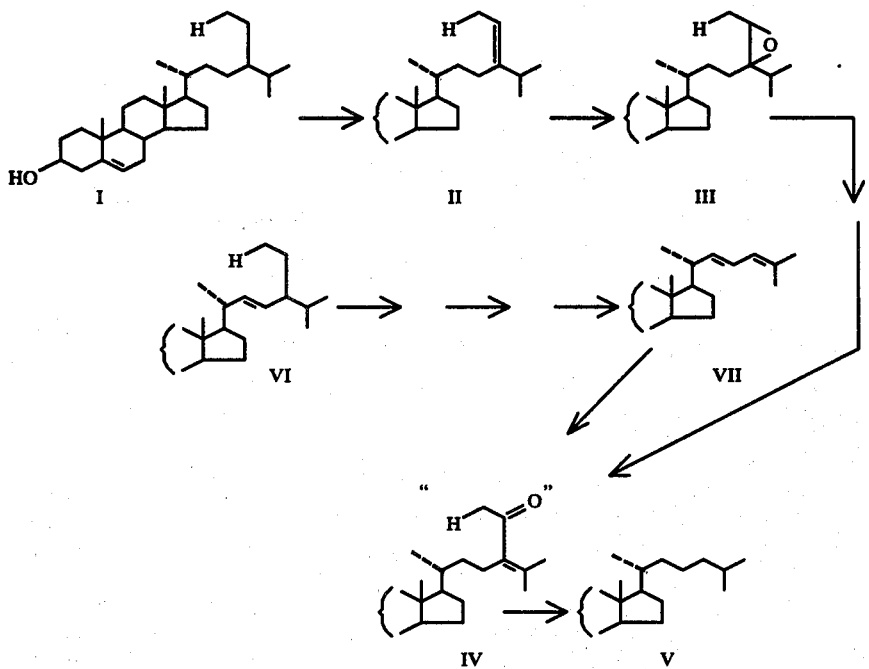

Scheme I those in the nest continue to multiply and thus the infestation remains. A delayed onset of toxic effects would allow for the insects to return poisoned food to the entire colony and thereby poison all the occupants. Thus in addition to high toxicity, an effective termite and insect pest poison must have a delayed onset of activity and be easily transferably to other members of a given colony.

Furthermore, an effective pesticide must possess the more subtle characteristic of not only being a "non-repellent", but should most advantageously be an "attractant." This simply means that a feeding termite would not prefer another food source over the poisoned source and ideally would even prefer the poisoned source over a regular food supply. Additional characteristics of an ideal pesticide would be nonleachability, i.e. poor solubility in water, and stability, i.e., but readily degraded in the soil.

BRIEF DESCRIPTION OF THE DRAWING

A complete understanding of the invention may be had from the foregoing and following description thereof, taken together with the appended drawing, in which.

DESCRIPTION OF THE INVENTION

Figure 1:
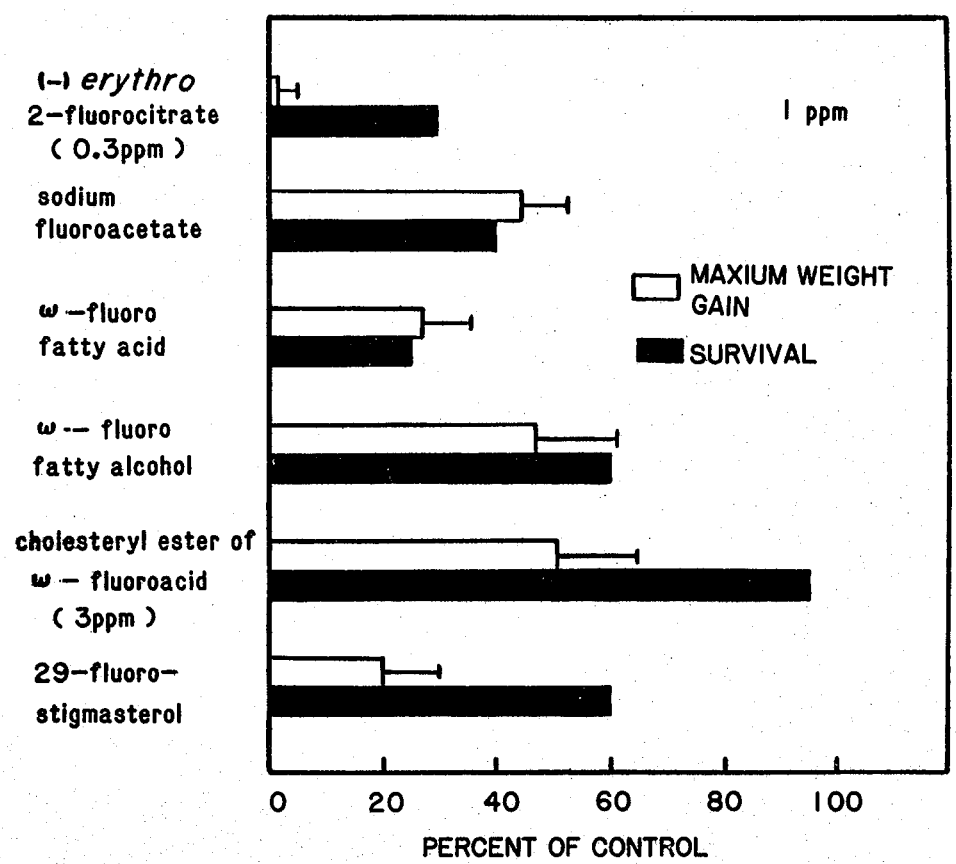
FIG. 1 shows the mean survival, weightgain, and developmental periods of the experimental hornworms relative to a group of twenty-control larvae.

The present invention relates to 29-fluorophytosterols and compositions containing same for the combatting of termites and related insect pests.

Preferred compounds of this invention are those selected from the group consisting of 29-fluorositosterol having the formula:

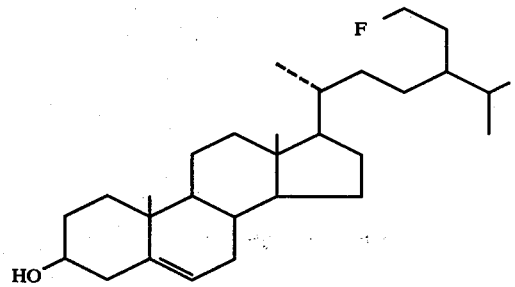

29-fluorostigmasterol having the formula:

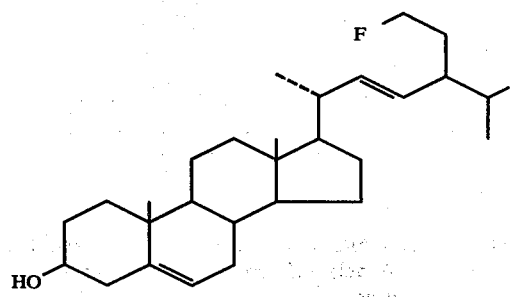

29-fluoroclionosterol having the formula:

29-fluoroporiferasterol having the formula:

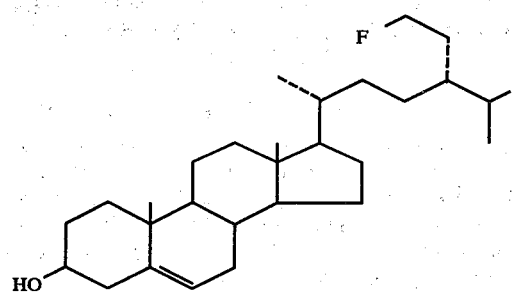

29-fluorofucosterol having the formula:

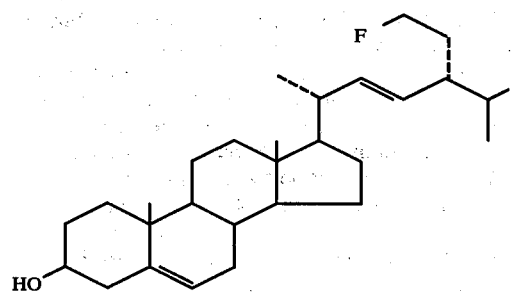

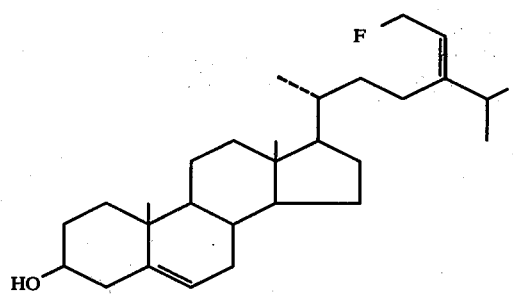

The 29-fluorophytosterols of this invention have been found to be effective termiticidal and insecticidal agents useful for the combatting of such pests. Thus, when a insecticidal or termiticidal amount of the 29-fluorophytosterol is combined with a solid carrier ingestible by termites or other insect pests a composition is formed which can be utilized to combat termites and other insect pests.

The compounds and compositions of the present invention possess the desirable attributes necessary for a safe, effective termiticide or insecticide. The compounds resemble normal steroids which makes them non-repellent and/or attractive. This steroid like character also makes them poorly soluble in water, so that they are substantially non-leachable, and stable, so that they are not readily degraded in the soil. Their metabolism by vertebrates does not proceed via dealkylation, so they are substantially non-toxic to vertebrates.

While in the preferred embodiments of this invention there are employed compounds having both attractant and termiticidal and insecticidal, properties the invention is not limited thereto.

The basic criteria is the active compound shall be termiticidal or insecticidal. It is required that the compounds employed be non-repellant to insects since insects will normally seek out regular food sources such as cellulosic materials, in particular wood, which can be treated with such termiticidal compositions. The provision of bait blocks treated with such compositions, for example, but of course not limited to, 29-fluorositosterol or 29-fluorostigmasterol are considered to be within the scope of the present invention.

It has been found advantageous to additionally provide such bait blocks comprising non-repellant termiticides or insecticides with an attractant composition attracting the termites or other insects. Such attractant compositions may either comprise a member of the 29-fluorophytosterols disclosed herein which have termiticidal or insecticidal as well as attractant properties or can also include any compounds known to the art which have the property of being attractive to termites or other insects.

When tested in standardized test procedures for insecticidal activity, the compounds and compositions of the present invention exhibit high toxicity vis a vis *Manduca secta*, the tobacco hornworm. Thus, they are insecticidal (toxic) at levels of about 1 to 100 mg/kg.

When tested in standardized test procedures for termiticidal activity, the compounds and compositions of the present invention exhibit high toxicity vis a vis *Reticulitermes flavipes*, the eastern subterranean termite. Thus, they are termiticidal (toxic) at levels of about 1 to 100 mg/kg, or 4 to 400 ng/termite. A small amount of 10–500 mg is thus capable of destroying a typical 60,000 termite mature colony. Additionally, they have a delayed onset of activity, exhibiting the toxic effects only after metabolism has begun.

The water insoluble solid carrier ingestible by termites utilized in the compositions of the present invention are cellulose based preferably wood, i.e. most preferably a block of wood, which may also be partially enclosed by a water-insoluble sheath such as a plastic sheath to further reduce leaching but leaving enough surface to which the termites would typically be attached.

The termiticidal, attractant and termiticidal attractive compounds disclosed and discussed herein, suitably the α-fluorophylosterol is applied to the carrier at a rate of about 0.05–1.0 percent (500 to 10,000 ppm). Preferably, they are applied to the carrier at a rate of about 0.5 to 1.0 percent (5000 to 10,000 ppm). Such application is very effective when carried out by vacuum treatment of the wood block with a solution of the active agent in a non-residual solvent, preferably acetone.

In addition, to *Reticulitermes flavipies*, the compounds and compositions of the present invention are useful in combatting *Coptotermes formosanus* (Formosan termite) as well as other European, Asian, African, and South American pest termites. Typically, the α-fluorophytosterol is applied to a suitable carrier, i.e. small blocks of wood, which are then provided to the termites as a food supply. The feeding termites ingest the treated carrier, travel back to the colony and regurgitate the treated carrier. The nest inhabitants ingest the treated carrier, and all are thereby affected, thus destroying the colony population.

The 29-fluorophytosterols of this invention are conveniently prepared by reaction of the known A/B protected-29-alcohols of the formula:

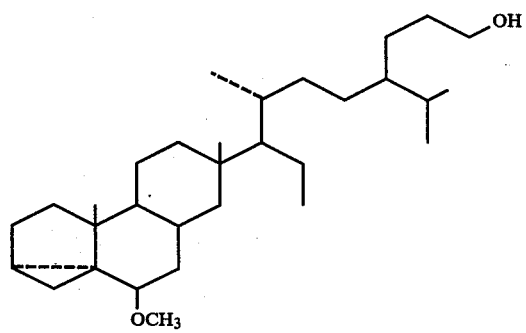

which may optionally contain one or more cis or trans double bonds in the oogoniol side chain and hav the R, S or R,S stereochemical configuration with a suitable fluorinating agent such as diethylaminosulfur trifluoride. The A/B-protected-29-alcohol starting materials are described in Djerassi et., al., *J. Org. Chem*, 44, 3372–3382 (1979) and Barrow and McMorris, *Lipids,* 17, 383–389 (1982). The fluorination procedure is substantially as described in Middleton, *J. Org. Chem*, 40, 574–578 (1975) and Haas and Gerstenberger, *Angew. Chem. Int. Ed. Engl.,* 20, 647–667 (1981). Typically, the reaction is conducted in an anhydrous solvent, such as tetrahydrofuran at a low temperature (about −78° C.).

The resultant A/B-protected 29-fluoro compound of the formula

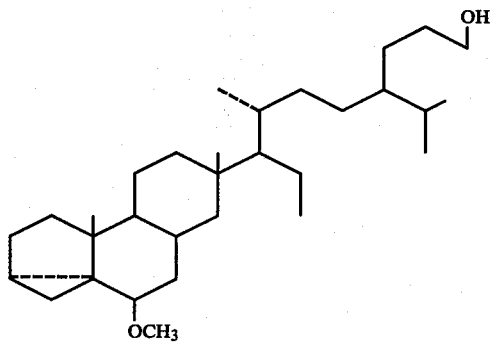

which may optionally contain one or more cis or trans double bonds in the oogonial side chain and have the R,S or RS stereochemical configuration is then deprotected using water and a catalytic amount of p-toluenesulfonic acid to afford the desired 29-fluorophytosterols.

Alternatively, the A/B-protected-29-alcohols can be produced by the following reaction Scheme II:

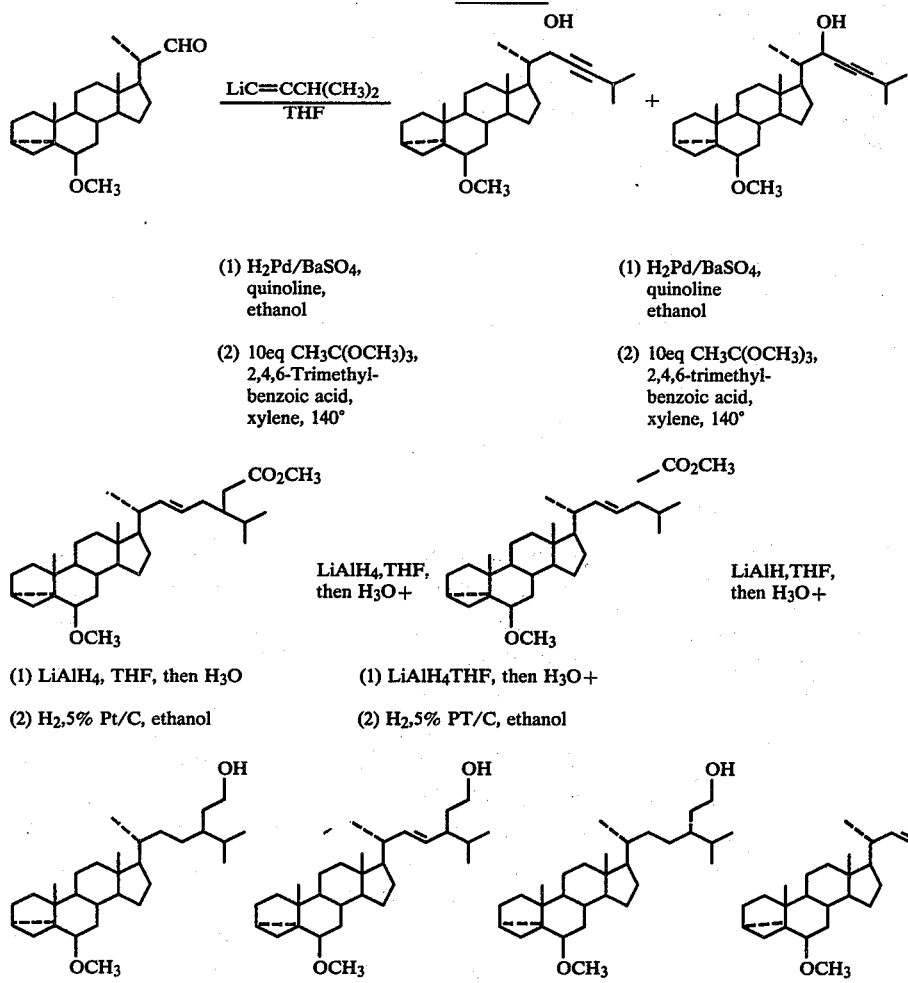

INSECTICIDE BIOASSAY OF 29-FLUOROPHYTOSTEROLS

The recrystallized 29-fluorosterols are dissolved in dichloromethane and then coated onto the wheat germ to give a final concentration to 50 ppm (w/v) in the articifical diet. Controls receive either 50 ppm of stigmasterol or no additional sterols. The dose are varied in subsequent experiments. Twenty first instar tobacco hornworms larvae (*Manduca sexta*, seventh day after egg collection) are then placed on a 0.5-g slab of diet in a 1-oz dish; this is designated as Day 0 of feeding. Larvae were maintained at 65% relative humidity and 26° C. on a 17L/7D long day light regime. Diets are changed and larvae are weighed and staged daily. The mean survival, weight gain, and developmental periods of the experimental hornworms are shown relative to a group of twenty control larvae in FIG. 1.

Four gut-purged prepupae from each experiment are frozen and later are analyzed individually for sterol composition. Each hornworm is homogenized (1:1 chloroform-methanol), the lipids is saponified, and the non-saponifiable lipis are chromatographed to give the sterol fraction. Analysis by capillary GC (Durabon DB-5 or DB-1701) allowed resolution an accurate quantification of cholesterol, desmosterol, campesterol, sitosterol and fucosterol from test insects. The results, present in Table 1, illustrate the insect metabolism.

TABLE 1

Sterol distribution in experimental hornworms. Values are means of relative area % of the gas chromatograms for each of 4 hornworms + 1 S.D.. All compounds were fed at 50 ppm. No survivors fed 29-fluorostigmasterols were present for analysis.

| Compound | RELATIVE PERCENT STEROL | | | |
| --- | --- | --- | --- | --- |
|  | Cholesterol | Desmosterol | Campesterol | Sitosterol |
| 29-fluorositosterol | 82.4(8) | 5.2(8) | 7.8(3) | 4.6(4) |
| 29-fluorostigmasterol | — | — | — | — |
| 29-fluoroclionosterol | 82.5(2) | 2.0(2) | 9.5(1) | 5.9(1) |
| 29-fluoroporiferasterol | 65.6(8) | 5.8(2) | 16.3(2) | 12.3(5) |
| 29-fluorofucosterol | 82.2(2) | 1.0(1) | 10.0(2) | 5.8(2) |

The dose-response data obtained from log concentration-probit resonse plots for compounds is summarized in Table 2.

TABLE 2

$EC_{50}$ and $LC_{50}$ values

Inequality signs indicate that the effect indicated was beyond the range of doses tested and could not be reliably obtained by extrapolation of the log concentration vs. probit response plots. All values are reported as parts per million (w/v) in the final diet.

|  | Dose for 50% Reduction | | |
| --- | --- | --- | --- |
|  | Maximum Larval Weight (EC$_{50}$) | Survival (Larvae, Day 21) (LC$_{50}$) | Pupation (EC$_{50}$) |
| 29-fluorositosterol | 110 ppm | 300 ppm | 150 ppm |
| 29-fluorostigmasterol | 1 | 4 | 1 |
| 29-fluorofucosterol | 26 | 48 | 31 |

Termiticide Bioassay of fluorophytosterols (Petri Dish Assay)

Test compounds are dissolved in dry diethyl ether or dichloromethane and a 1.0 ml portion of the solution is pipetted onto a Gelman sterile 47-mm cellulose pad (Howard & Haverty, 1979). The ether is allowed to evaporate for 10 min, 1.0 ml of distilled water was added to the pad, and the pad is placed in a tight-sealing Gelman 50-mm plastic Petri dish.

Termites (*Reticulitermes flavipies* Kollar) are collected from rotten logs and three stumps. Colonies are kept in trash cans in an insectary (85% RH, 27° C.) for a period of about 6 months before use. The experiments are performed in an incubator at +28° C. Undifferentiated larvae above the third instar ("workers") are used in all toxicity tests. Termites are first shaken loose from the interior of the wood, then transferred using mouth aspirators and with soft forceps. The termites are held on filter papers for 24 hours, twenty healthy termites are added to each dish, and the number of dead (removed to prevent cannibalism) is recorded at daily intervals.

EXPERIMENTAL

The following examples describe in detail compounds and compositions illustrative of the present invention and methods which have been devised for their preparation. It will be apparent to those skilled in the art that many modifications, both of materials and methods, may be practiced without departing from the purpose and intent of this disclosure.

Unless otherwise noted, materials are obtained from commercial suppliers and are used without further purification. Tetrahydrofuran (THF, Aldrich Gold Label) (is distilled from sodium benzophenone in a circulating still, with a deep blue color being maintained in the distilling pot. Hexamethylphosphoric triamide (HMPA) is distilled from BaO and stored over molecular sieves (3Å). Acetone is dried over potassium carbonate distilled and stored over molecular sieves (3Å). Pyridine is dried over sodium hydroxide, distilled from BaO and stored over molecular sieves (3Å). Hexane, ethyl acetate and methanol are Fisher HPLC grade and are used without further purification. p-Toluenesulfonyl chloride is recrystallized from chloroform/petroleum ether (1:5 v/v). Toluene is dried by azeotropic distillation. Acetonitrile is distilled from calcium hydride. All reactions are performed under a nitrogen atmosphere.

H NMR spectra are recorded on a Varian HFT-80- (80 MHZ) spectrometer in deuterochloroform with tetramethylsilane as the internal standard. Data are reported in the form of $\delta$ values of signal (peak multiplicity, coupling constant, if appropriate, numbers of protons). When peak multiplicities are reported, the following abbreviations are used: s, singlet; d, doublet; t, triplet; q, quarter; m, multiplet; br, broaden. $^{13}$C NMR spectra are recorded on a Varian CFT-20 (20 MHZ) spectrometer and proton noise decoupling and shifts are reported relative to tetramethylsilane ($\delta$=0.ppm). Data are reported in the form of $\delta$ values of signal (peak multiplicity, and coupling constant if appropriate, intensity). Infrared spectra are obtained on a Perkin Elmer 727 instrument as a neat liquid. Data are given in cm$^{-1}$ with only the important diagnostic values reported.

Thin layer chromatography is performed by using MN Polygram Sil G/UV 254 (4×8) TLC plates. Visualization accomplished by UV light, iodine, or an ethanol-vanillin-H$_2$SO$_4$ reagent. Flash chromatography (Still et al., *J. Org. Chem.*, 43, 2923, 1978) is performed under N$_2$ pressure on Merck Silica Gel G (400–230 mesh) using hexane/ethyl acetate mixtures. Analytical gas-liquid chromatography (GC) is performed on a Varian model 3700 chromatograph (programmable temperature control) equipped with a flame ionization detector and nitrogen carrier gas.

EXAMPLE 1

29-Fluoro-(22E, 24S)-6$\beta$-methoxy-3$\alpha$,5-cyclo-5$\alpha$-stigmast-22-ene A solution of 29-hydroxy-(22E, 24S)-6$\beta$-methoxy-3$\alpha$,5-cyclo-5$\alpha$-stigmast-22-ene(preparable according to the method of Djerassi et.,al., J. Org. Chem., 44, 3372–3382 (1979)) (182.4 mg. 0.41 moles), in 5mL of dry tetrahydrofuran is slowly added to a solution of diethylaminosulfur trifluoride (DAST) (66 mg. 0.41 moles), in 5 ml of tetrahydrofuran at −78° C. The mixture is allowed to come to room temperature and stirred for 3 hours. Solid sodium carbonate is added followed by 5% aqueous sodium bicarbonate. The organic layer is then extraced with ethyl acetate, dried over magnesium sulfate and chrmoatographed (1% ethylacetate/-hexane) to give 29-fluoro-(22E,24S)-6$\beta$-methoxy-3$\alpha$,5-cyclo-5$\alpha$-stigmast-22-ene (89.6 mg., 0.20 mmoles), as an oil, having the following characteristics: $^1$H-NMR$\delta$0.30–0.60 (2H,m,4-H), 0.72 (3H,s,18-CH$_3$) 0.82 (3H,d,26-CH$_3$, j=6.6 Hz), 0.86 (3H,d,27-CH$_3$,J=6.4 Hz), 1.00 (3H,d,21-CH$_3$,J=6.5 Hz), 1.01 (3H,s,19-CH$_3$), 2.76 (1H,m,6-H) 3.31 (3H,s,OCH$_3$), 4.39 (2H,d of m, 29-CH$_2$F,J=46.8 hz), 5.12 (2H, m.220 and 23-H); mass spectrum 20.21,28, calc. 444:3768, found 444.3835; m/z (% Rel. int.) 429 (38, M-CH$_3$), 412 (32,M-CH$_3$CH), 397 (12,M-CH$_2$CH$_2$F), 389 (65,M-C$_4$H$_7$, ring A fission), 255 (63,M-side chain +MeOH), 253 (40.M-CH$_3$OH+side chain+2H), 213 (35.M-CH$_3$OH+ring D fission +1H), 81 (100.C$_6$H$_9$).

EXAMPLE 2

29-Fluoro-(22E,24R)-6$\beta$-methoxy-3$\alpha$,5-cyclo-5$\alpha$-stigmanst-22-ene In a similar manner, treatment of 29-hydroxy-(22E, 24R)-6$\beta$-methoxy-3$\alpha$,5-cyclo-5$\alpha$-stigmast-22-ene (125 mg, 0.28 mmoles) with diethylaminosulfur trifluoride (45.5 mg, 0.28 mmoles) according to the procedure detailed in Example 1, gives, after workup and chromatography, 29-fluoro-(22E,24R)-6$\beta$-methoxy-3$\alpha$,5-cyclo-5$\alpha$-stigmast-22-ene (77 mg., 0.17 mmoles), as a noncrystalline material having the following characteristics:

$^1$H-NMR$\delta$0.30-0.60 (2H,m,4-H), 0.77 (3H,s,18-CH$_3$), 0.81 (3H,d,26-CH$_3$,J=6.5 Hz), 0.86 (3H, d,27-CH$_3$, J=6.3 Hz), 1.00 (3H, d, 21, CH$_3$, J=6.5 Hz), 1.01 (3H, s,19,Ch$_3$), 2.76 (1H,m,6-H), 3.31 (3H,s,-OCH$_3$), 4.38 (2H,d,of m,29-CH$_2$F,J=46.8 Hz), 5.16 (2H,m,22-H and 23-H) mass spectrum 20,21,28 calc. 444.3767, found 444.3765; m/z (%Rel. int.) 444 (10,M$^+$) rest of spectra similar to those of 29-fluoro-(22E, 24S)-6β-methoxy-3α,5-cyclo-5α-stigmast-22-ene.

EXAMPLE 3

29-Fluoro-(24S)-6β-methoxy-3α,5-cyclo-5α-stigmastane

Repetition of the procedure detailed in Example 1 using 29-hydroxy-(24S)-6β-methoxy-3α,5-cyclo-5β-stigmastane (preparable according to the method of Djerassi et. al., J.Org. Chem., 44, 3372–3382 (1979)), as starting material affords 29-fluoro-(24S)-6β-methoxy-3α,5-cyclo-5α-stigmastane having the following characteristics: $^1$H-NMR (CDCl$_3$, 80 MHz) δ0.30–0.60 (m, H-4), 0.71 (s, CH$_3$-18), 0.84 (d, CH$_3$-26, CH$_3$-27, J=6.5 Hz, coincidental overlap), 0.97 (d, CH$_3$-21, J=5.8 Hz), 1.01 (s, CH$_3$-19), 2.75 (m, H-6), 3.32 (s, OCH$_3$), 4.42 (d of m, H-29, J$_{HF}$=46.8 Hz).

EXAMPLE 4

29-Fluoro-(24R)-6β-methoxy-3α,5-cyclo-5α-stigmastane

Substantially repeating the procedure detailed in Example 1, utilizing 29-hydroxy-(24R)-6β-methoxy-3α,5-cyclo-5α-stigmastane (preparable according to the method of Djerassi et., al., *J. Org. Chem*, 44 3372–3382 (1979)), as starting material affords 29-fluoro-(24R)-6β-methoxy-3α,5-cyclo-5α-stigmastane, as an oil, having the following characteristics: $^1$H-NMR as for the compound of Example 3, except δ4.46 (d of m, H-29, J$_{HF}$=47.3 Hz).

EXAMPLE 5

29-fluoro-(24Z)-6β-methoxy-3α,5-cyclo-5α-stigmast-24ene

Substantial repetition of the procedure of Example 1 utilizing 29-fluoro-(24Z)-6β-methoxy-3,5-cyclo-5α-stigmast-24-ene) (preparable according to the procedure of Barrow and McMorris, *Lipids,* 17, pp 383–389 (1982)), affords 29-fluoro-(24Z)-6β-methoxy-3α,5-cyclo-5α-stigmast-24-ene.

EXAMPLE 6

29-fluorostigmasterol

To a solution of 29-fluoro-(22E,24S)-6β-methoxy-3α,5-cyclo-5α-stigmast-22-ene (preparable as described in Example 1) (70 mg, 0.16 mmoles), in 5 mL of dioxane is added water, until the solution becomes cloudy. A small crystal of p-toluenesulphonic acid is then added and the mixture refluxed for about 3 hrs. More water is added until the hot solution just becomes cloudy. The solution is then allowed to cool to room temperature. Filtration and recrystallization from methanol gives 29-fluoro-stigmasterol (50 mg, 0.12 mmoles), having the following characteristics: mp 131°–132°, $^1$H-NMR δ0.69 (3H,s,18-CH$_3$), 0.83 (3H,d,26-CH$_3$,J=6,8 Hz), 0.88 (3H,d,27-Ch$_3$, J=6.4 Hz), 1.00 (3H,s,19-CH$_3$), 1.01 (3H,d,21-CH$_3$, J=6.6 Hz), 3.5(1H,m,3-H), 4.39 (2H.d of m, 29-CH$_2$F,J=46.8 Hz), 5.12 (2H,m,22-H and 23-H), 5.25 (1H,m,6-H); mass spectrum 20,21,28, calc. for C$_{29}$H$_{47}$ OF 430.3610 found 430.3571; m/z (%Rel. int.) 430 (34.M+), 412 (10,M-H$_2$O), 397 (5,M-CH$_3$+H$_2$0), 345 (5.M-complex A and B ring fission), 300, (21, M-C(20)-C(22) fission +H), 273 (10,M-side chain fission), 271 (20, M-side chain fission +2H), 255 (43, M-side chain fission +H$_2$O), 213 (32,M-ring D fission +H$_2$O+1H), 133 (10001).

EXAMPLE 7

29-Fluoroporiferasterol

Treatment of 29-fluoro-(22E,24R)-6β-methoxy-3α,5-cyclo-5α-stigmast-22-ene (preparable as described in Example 2) (50 mg 0.11 mmoles) according to the procedure detailed in Example 6, gives, after filtration and crystallization, 29-fluoroporiferasterol, having the following characteristics: mp 125°–128° C. (meOH): $^1$H-NMR δ0.69 (3H,s,18-CH$_3$), 0.82 (3H,d,26-CH$_3$, J=6.5 Hz), 0.87 (3H,d,27-CH$_3$, J=6.4), 1.00 (3H,s,19-CH$_3$), 3.50 (1H,m,3-H), 4.39 (2H,d of m, 29-CH$_2$F, J=46.8 Hz), 5.12 (2H,m,22-H and 23-H), 5.25 (1H,m,6-H); mass spectrum 20,21,28, calc. for C$_{29}$H$_{47}$OF 430.3611, found 430.3599; rest of spectra similar to those of 29-fluorostigmasterol.

EXAMPLE 8

29-Fluorositosterol

Repetition of the procedure detailed in Example 6 utilizing 29-fluoro-(24S)-6β-methoxy-3α,5-cyclo-5α-stigmastane (preparable as described in Example 3) as starting material, affords 29-fluorositosterol, having the following characteristics: $^1$H-NMR, (300 MHz, δ0.067 (s, CH$_3$-18), 0.83 (d, Ch$_3$-26, J=6.8 Hz), 0.84 (d, CH$_3$-27, J=6.8 Hz), 0.91 (d, CH$_3$-21, J=6.5 Hz), 0.99 (s, CH$_3$-19), 3.51 (m, H-3), 4.45 (d of m, H-29, J$_{HF}$=47.3 Hz), 5.34 (m, H-6); $^{13}$C-NMR (CDCl$_3$, 75 MHz), δ31.40 (d, 18.2 Hz, C-28), 40.29 (d, 4.4 Hz, C-24), 83.43 (d, 163.9 Hz C-29); LRMS: m/z (rel. int.) 432 (18, M+), 414 (15, M-H$_2$O), 399 (17, M-CH$_3$-H$_2$O), 347 (22), 273 (15), 255 (26), 213 (48), 107 (100); HRMS, calcd for C$_{29}$H$_{49}$OF, 432.3768; found, 432.3793.

EXAMPLE 9

29-Fluoroclionosterol

Utilizing 29-fluoro-(24R)-6β-methoxy-3α,5-cyclo-5α-stigmastane (preparable as described in Example 4) as starting material and substantially repeating the procedure detailed in Example 6 affords 29-fluoroclionosterol, having the following characteristics: $^2$H-NMR (300 MHZ) as the compound of Example 8 except δ4.47 (d of m, H-29, J=46.5 Hz), $^{13}$C-NMR (20 MHz), δ31.5 (d,19.2 Hz, C-28) 40.4 (d, 5.2 Hz, C-24), 82.8 (d, 164.0 Hz, C-29).

EXAMPLE 10

29-Fluorofucosterol

Substantial repetition of the procedure of Example 6 utilizing 29-fluoro-(22Z)-6β-methoxy-3α,5-cyclo-5α-stigmast-24-ene (preparable as detailed in Example 5) as the starting material, affords 29-fluorofucosterol.

EXAMPLE 11

Preparation of Bait Blocks

29-Fluorostigmasterol is dissolved in acetone as a 0.1, 0.05, 0.01 percent solution.

Oven dried wood blocks are vacuum impregnated in the solution in accordance with the method of Maudlin & Rich (*J. Econ. Entomol* 73 123 (1980)).

The wood blocks are heated to 50° C. for 24 hours and fixed to the bottom of a container. The container is depressurized down to 100 mm Hg for 20 minutes and the blocks allowed to cool. While still under vacuum, the container is flooded with fluoroalkanol/acetone solution to sufficient depth to submerge the blocks. The vacuum is then released and the blocks permitted to soak for 30 minutes. The blocks are then removed from the solution and permitted to dry under ambient conditions.

The blocks are utilized for burying under the soil in areas proximate to termite nests.

If desired the blocks may be partially encased in plastic to discourage the attention of larger animals.

Other cellulosic substrates such as paper, pressboard, cardboard, leaf litter or dry grass may be used as bait materials for coating or impregnation. This allows for the targeting of the toxicant to a variety of arboreal subterranean and mound-building tropical termites as well as the eastern subterranean termite *Reticulitermes flavipies* as mentioned above.

In accordance with the above procedure wood blocks may be similarly impregnated with:
29-fluorofucosterol,
29-fluoroporiferasterol,
29-fluoroclinosterol,
29-fluorositosterol,
or any of the 29-fluorophytosterols prepared in accordance with the present invention, to obtain a similar product.

What is claimed is:

1. A 29-fluorophytosterol of the formula:

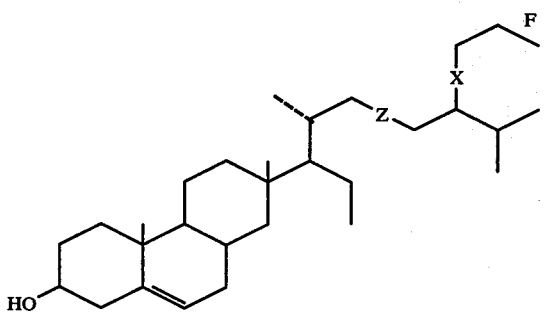

wherein —Z— or —X— may each be single or a cis, or a trans double bond provided only one thereof may be a double bond further provided that where X is a single bond it may be in the R,S or RS sterochemical conformation.

2. In accordance with claim 1 wherein —Z— or —X— is a double bond.

3. In accordance with claim 1 wherein —Z— or —X— is a single bond.

4. In accordance with claim 2 wherein —Z— or —X— is a trans double bond.

5. A compound according to claim 1 which is 29-fluorostigmasterol.

6. A compound according to claim 1 which is 29-fluorositosterol.

7. A compound according to claim 1 which is 29-fluoroclionosterol.

8. A compound according to claim 1 which is 29-fluoroporiferasterol.

9. A compound according to claim 1 which is 29-fluorofucosterol.

10. An insecticidal composition comprising an solid carrier ingestible by insects having absorbed thereon an insecticidally effective amount of a 29-fluorophytosterol of claim 1.

11. A termiticidal composition according to claim 10 comprising a water-insoluble solid carrier ingestible by termites, having absorbed thereon a termiticidally effective of an amount of a 29-fluorophytosterol of the formula of claim 1.

12. A composition of claim 11 additionally comprising a termite attractant composition.

13. A composition according to claim 11 wherein the 29-fluorophytosterol is 29-fluorositosterol.

14. A composition according to claim 11 wherein the 29-fluorophytosterol is 29-fluorostigmasterol.

15. A compression according to claim 11 wherein the 29-fluorophytosterol is 29-fluoroclionosterol.

16. A composition according to claim 11 wherein the 29-fluorophytosterol is 29-fluoroporiferasterol.

17. A composition according to claim 11 wherein the 29-fluorophytosterol is 29-fluorofucosterol.

18. A composition according to claim 11 wherein the water-soluble solid carrier is a cellulosic substrate.

19. A method of combatting insects which comprises providing an insecticidal composition according to claim 10 to a location proximate to insect nests.

20. A method of combatting termites which comprises providing a termiticidal composition according to claim 11 to a location proximate to termite nests.

21. A method of combatting termites which comprises providing a termiticidal composition according to claim 13 to a location proximate to termite nests.

22. A method of combatting termites which comprises providing a termiticidal composition according to claim 14 to a location proximate to termite nests.

23. A method of combatting termites which comprises providing a termiticidal composition according to claim 15 to a location proximate to termite nests.

24. A method of combatting termites which comprises providing a termiticidal composition according to claim 16 wherein the water-insoluble solid carrier is a cellulosic substrate.

25. A method of combatting termites which comprises providing a termiticidal composition according to claim 17 wherein the water-insoluble solid carrier is a cellulosic substrate.

* * * * *

UNITED STATES PATENT OFFICE
CERTIFICATE OF CORRECTION

Patent No. 4,452,793                    Dated June 5, 1984

Inventor(s)   Glenn D. Prestwich

It is certified that error appears in the above-identified patent and that said Letters Patent are hereby corrected as shown below:

Column 1, line 23, delete "product", insert --produce--.

Column 2, delete formula IV as shown, insert

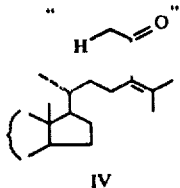

IV

Column 2, before line 64, insert
--The evidence for the steps indicated (dehydrogenation, epoxidation, fragmentation, and 24-reduction) has been summarized in several reviews.  See, for instance, Svoboda and Thompson, "Comparative steroid metabolism in insects", p. 1-16; and Morisaki et. al., "Sterol metabolism of the silkworm *Bombyx mori*", pp. 17-26; both in *Metabolic Aspects of Lipid Nutrition in Insects*, pp. 1-16, edited by Mittler and Dadd, Westview Press, 1983; Kircher, "Sterols and Insects", *in Cholesterol Systems in Insects and Animals*, edited by Dupont pp. 1-50, CRC Press, 1982; and Svoboda, *et. al.*, "Insect steroid metabolism", *Lipids* 13: 742-753 (1978).

Dealkylation is restricted to arthropods; however, not all insects possess this ability, nor do all insects employ the same steroid nucleus.  In general, phytophagous insects are capable of dealkylation while zoophagous insects lack this ability.
In contrast to arthropods, most other organisms -- from bacterial to mammals -- possess the ability to perform *de novo* steroid biosynthesis from mevalonate. Consequently, they lack the ability to dealkylate the $C_{29}$ phytosteroids.

UNITED STATES PATENT OFFICE
CERTIFICATE OF CORRECTION

Patent No. 4,452,793          Dated June 5, 1984

Inventor(s) Glenn D. Prestwich

It is certified that error appears in the above-identified patent and that said Letters Patent are hereby corrected as shown below:

For a pesticide to be effective against termites and related pests it must have a somewhat delayed onset of activity. Termites and other colony insects typically feast upon a food supply and then return to their nest to regurgitate the food to be shared by those occupying the nest. Thus, a pesticide which instantly destroys the feeding insect has absolutely no effect upon those hatching in the nest. While the feeding insects are affected,--

Column 4, line 67, delete "criteria" insert --criterion--.

Column 5, line 50, delete "9", insert --29--
          line 58, delete "flavipies", insert --flavipes--.
          line 62, delete "9", insert --29--.

Column 6, after line 7, delete the formula, insert:

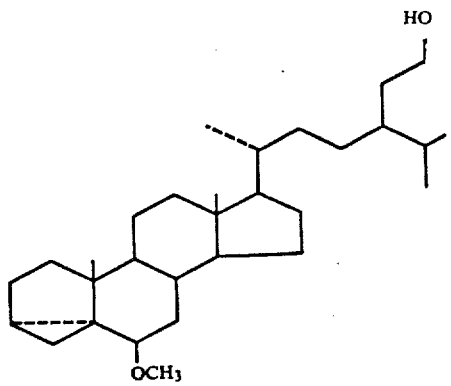

UNITED STATES PATENT OFFICE
CERTIFICATE OF CORRECTION

Patent No. 4,452,793     Dated June 5, 1984

Inventor(s): Glenn D. Prestwich

It is certified that error appears in the above-identified patent and that said Letters Patent are hereby corrected as shown below:

Column 6, after line 42, delete the formula, insert:

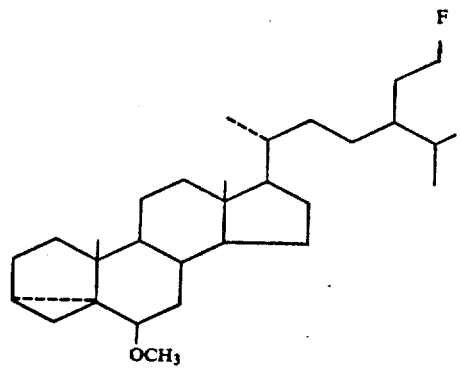

UNITED STATES PATENT OFFICE

CERTIFICATE OF CORRECTION

Patent No. 4,452,793    Dated June 5, 1984

Inventor(s) Glenn D. Prestwich

It is certified that error appears in the above-identified patent and that said Letters Patent are hereby corrected as shown below:

Columns 7 & 8, Delete the reaction chart as shown, insert:

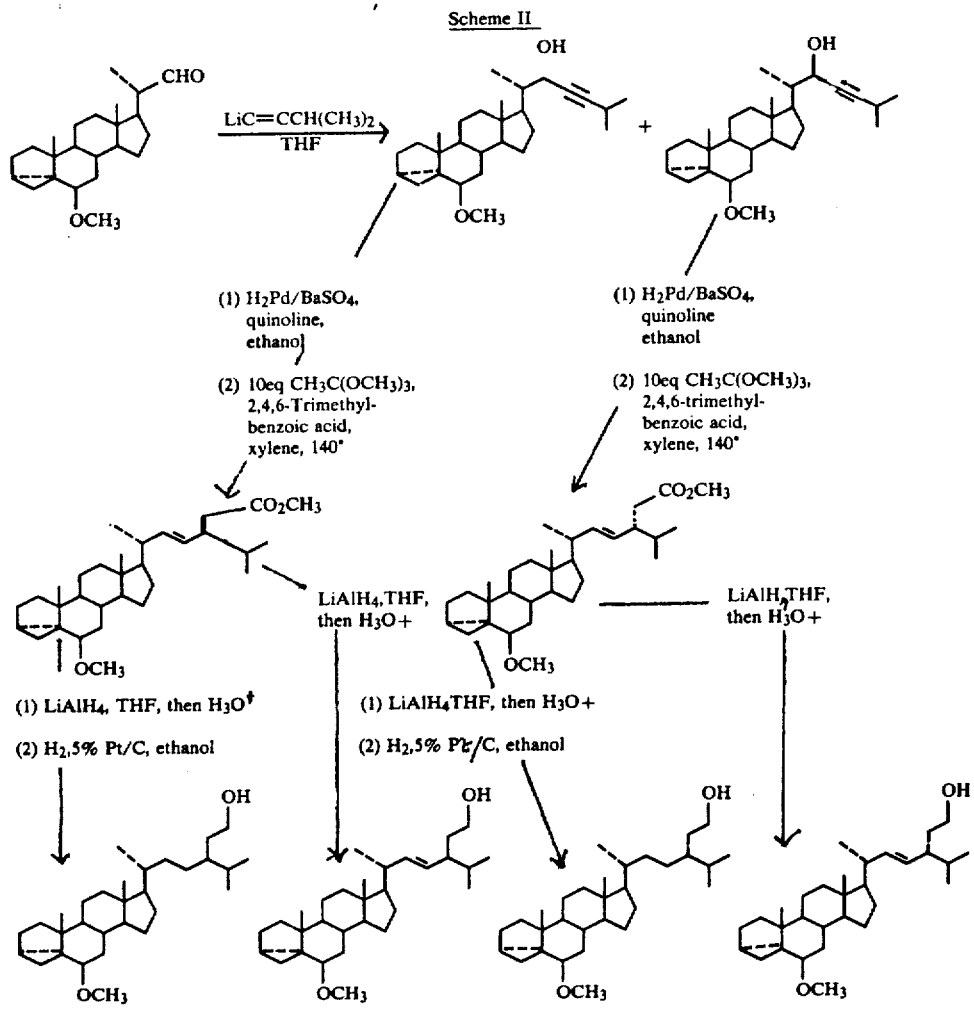

UNITED STATES PATENT OFFICE
CERTIFICATE OF CORRECTION

Patent No. 4,452,793             Dated June 5, 1984

Inventor(s) Glenn D. Prestwich

It is certified that error appears in the above-identified patent and that said Letters Patent are hereby corrected as shown below:

Column 7, line 48, delete "to" insert --of--.
         line 49, delete "articifical", insert --artificial--.
         line 52, delete "hornworms", insert --hornworm--.
         line 64, delete "is", insert --are--.
         line 65, delete "lipis", insert --lipids--.
         line 66, delete "Durabon", insert --Durabond--.

Column 8, line 43, delete "present", insert --presented--.
         line 59, delete "resonse" insert --response--.
         line 59, delete "is" insert --are--.

Column 9, line 20, delete "flavipies", insert --flavipes--.

Column 10, line 32, delete "extraced", insert --extracted--.
          line 33, delete "chrmoatographed", insert --chromatographed--.

Column 13, line 15, delete "flavipies", insert --flavipes--.

UNITED STATES PATENT OFFICE
CERTIFICATE OF CORRECTION

Patent No. 4,452,793  Dated June 5, 1984

Inventor(s) Glenn D. Prestwich

It is certified that error appears in the above-identified patent and that said Letters Patent are hereby corrected as shown below:

In the Claims

Claim 1, delete the structural formula, and insert in place thereof:

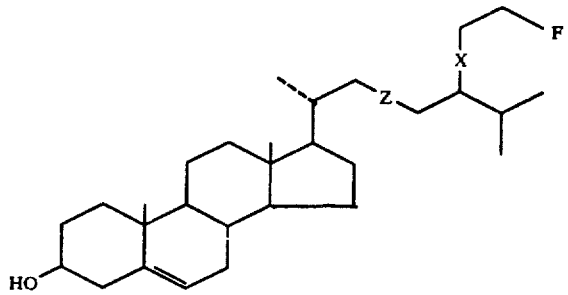

Claim 15, delete "compression" insert --composition--.

Signed and Sealed this

Twenty-first Day of May 1985

[SEAL]

Attest:

DONALD J. QUIGG

Attesting Officer   Acting Commissioner of Patents and Trademarks